United States Patent [19]

Merger et al.

[11] 4,282,370

[45] Aug. 4, 1981

[54] PREPARATION OF METHYLENE-BIS-PHENYLCARBAMIC ACID ESTERS AND OF POLYMETHYLENE-POLYPHENYLCARBAMIC ACID ESTERS

[75] Inventors: Franz Merger, Frankenthal; Gerhard Nestler, Ludwigshafen, both of Fed. Rep. of Germany

[73] Assignee: BASF Aktiengesellschaft, Fed. Rep. of Germany

[21] Appl. No.: 166,568

[22] Filed: Jul. 7, 1980

[30] Foreign Application Priority Data

Aug. 3, 1979 [DE] Fed. Rep. of Germany ....... 2931554

[51] Int. Cl.³ ................ C07C 125/073; C07C 118/00; C07C 119/048
[52] U.S. Cl. .................................. 560/25; 260/453 P
[58] Field of Search .......................................... 560/25

[56] References Cited

U.S. PATENT DOCUMENTS

| 2,946,768 | 7/1960 | Klauke et al. | 560/25 |
| 4,146,727 | 3/1979 | Shawl et al. | 560/25 |
| 4,162,362 | 7/1979 | Shawl | 560/25 |
| 4,163,019 | 7/1979 | Mango | 560/25 |
| 4,202,986 | 5/1980 | Shawl | 560/25 |
| 4,230,877 | 10/1980 | Shawl et al. | 560/25 |

*Primary Examiner*—G. T. Breitenstein
*Attorney, Agent, or Firm*—Keil & Witherspoon

[57] ABSTRACT

A process for preparing a methylene-bis-(4-phenylcarbamic acid ester), wherein an N-phenylcarbamic acid ester is reacted with an acylal in the presence of an acid at from 50° to 150° C.

4 Claims, No Drawings

PREPARATION OF METHYLENE-BIS-PHENYLCARBAMIC ACID ESTERS AND OF POLYMETHYLENE-POLYPHENYLCARBAMIC ACID ESTERS

The present invention relates to a novel process for preparing methylene-bis-phenylcarbamic acid esters and of polymethylene-polyphenylcarbamic acid esters by reacting an N-phenylcarbamic acid ester with an acylal in the presence of an acid.

Methylene-bis-phenylcarbamic acid esters and higher homologs thereof are valuable starting materials for the preparation of methylene-bis-phenylisocyanates and of the corresponding polymethylene-polyphenylisocyanates; the use of these for the preparation of polyurethanes has been disclosed (German Laid-Open Application DOS No. 2,635,490). The commercially available isocyanates of this type are in general prepared by phosgenating the amines obtained by condensing aniline with formaldehyde in the presence of an aqueous acid.

Methylene-bis-phenylcarbamic acid esters are obtained by reacting the aniline-formaldehyde condensate with a chloroformic acid ester in the presence of a base, or by reacting the corresponding isocyanate with an alcohol.

These processes have the disadvantage that, for safety reasons, the reaction with phosgene, a highly toxic compound, entails an expensive technology. Furthermore, the removal of the acids which, on the one hand, are required in the various reactions and, on the other hand, are formed as by-products, greatly pollutes the environment.

Methylene-bis-phenylcarbamic acid esters can also be prepared by reacting methylene-bis-nitrophenyl with an alcohol and carbon monoxide (cf. German Published Application DAS No. 1,568,044). Since the preparation of the requisite nitro compounds is very difficult, this process has not acquired any industrial importance.

U.S. Pat. No. 2,946,768 proposes preparing the desired carbamic acid esters by condensing a phenylcarbamic acid ester with formaldehyde or with a formaldehyde donor in the presence of an aqueous acid. In this conventional process, the formaldehyde tends to react at the nitrogen of the carbamic acid ester, so that 15–50% by weight of undesired N-C-bonded products are formed (cf. German Published Application DAS No. 2,837,379, page 3, lines 5 to 13). A Comparative Example (see Example 1 below) carried out similarly to Example 2 of U.S. Pat. No. 2,946,768 confirms this state of affairs. Furthermore, other by-products are also formed, for example amines which are produced by acid hydrolysis of the carbamic acid ester.

Since there is no process by means of which the nitrogen-bonded products, which on pyrolysis do not give isocyanates, might be separated off, the reaction mixtures prepared by the process of U.S. Pat. No. 2,946,768 are unsuitable for the preparation of isocyanates. Hence, this process is technically and economically unsatisfactory.

German Laid-Open Application DOS No. 2,832,379 describes a process for rearranging these undesired by-products to give methylene-bis-phenylcarbamic acid esters and higher homologous polymethylene-polyphenylcarbamic acid esters, derived therefrom. In this process, the reaction mixtures prepared by the process of U.S. Pat. No. 2,946,768 are reacted with strong proton acids or Lewis acids under virtually anhydrous conditions at 50°–170° C.

This technically difficult two-stage process is disadvantageous because initially a condensate is prepared, in accordance with U.S. Pat. No. 2,946,768, from the phenylcarbamic acid ester and formaldehyde solution in the presence of a large amount of an aqueous acid, and this condensate has to be freed from the acid and dried, whilst finally the reaction is carried out under anhydrous conditions again using a large amount of an acid, which must be removed completely at the end of the reaction. The amounts of acid involved, and the by-products formed, such as the amines resulting from hydrolysis by acid, result in serious pollution of the effluent.

We have found that the above difficulties in preparing methylene-bis-phenylcarbamic acid esters and polymethylene-polyphenylcarbamic acid esters can be avoided if an N-phenylcarbamic acid ester is reacted with an acylal of the formula $$CH_2(OCOR)_2$$

where R is alkyl, in the presence of an acid at from 50° to 150° C.

Using this novel process, the methylene-bis-phenylcarbamic acid esters and polymethylene-polyphenylcarbamic acid esters are obtained from N-phenylcarbamic acid esters by a surprisingly smooth one-stage reaction, in good yield and high purity.

In the case of the preparation of the methylene-bis-(4-phenylcarbamic acid ester) from methyl N-phenylcarbamate and diacetoxymethane, the reaction can be represented by the following equation:

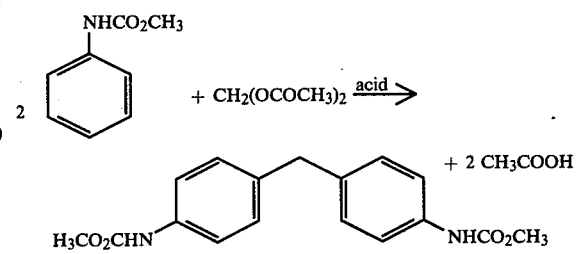

The process according to the invention also leads to the formation of higher homologous polymethylene-polyphenylcarbamic acid esters, ie. carbamic acid esters in which 3 or more benzene rings are joined to one another by methylene bridges, since the acylals also react, to a lesser degree, with methylene-bis-phenylcarbamic acid ester which has already been formed.

Examples of suitable N-phenylcarbamic acid esters are compounds of the formula

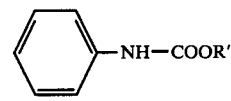

where R' is alkyl of 1 to 3 carbon atoms and the phenyl radical may be substituted in the o- and/or m-positions, for example by methyl or methoxy or by halogen, eg. by chlorine or bromine.

Specific examples of suitable N-phenylcarbamic acid esters are methyl, ethyl and propyl N-phenylcarbamic, methyl and ethyl N-o-tolylcarbamate, methyl N-2,6- dimethylphenylcarbamate and ethyl N-o-chlorophenylcarbamate.

The acylals form virtually no free formaldehyde under the reaction conditions and ensure that no water of reaction is formed in the reaction according to the invention. Preferably, the alkyl radical in the acylal corresponds to the alkanol on which the carbamic acid ester is based.

Diacetoxymethane is an example of a suitable acylal.

The reaction of the starting materials is carried out in the presence of an acid at from 50° to 150° C., preferably from 90° to 140° C., especially from 90° to 120° C.

The molar ratio of acylal to carbamic acid ester is in general from 1:0.5 to 1:10, preferably from 1:1.5 to 1:3. If the intention is principally to prepare methylene-bis-phenylcarbamic acid ester, substantially avoiding the formation of polymethylene-polyphenylcarbamic acid esters, the above ratio is preferably from 1:4 to 1:8.

Examples of suitable acids, which are used in amounts of, for example, from 1 to 100, preferably from 10 to 60, mole% based on carbamic acid ester, are phosphoric acid, sulfuric acid, an alkylsulfonic acid, eg. methanesulfonic acid, or an arysulfonic acid, eg. p-toluenesulfonic acid. According to a particularly advantageous embodiment of the invention, a strong acid which can be removed from the reaction mixture by distillation, for example trifluoromethanesulfonic acid, is used. This dispenses with having to work up the reaction mixture with water or with a base, and the acid can directly be recycled to the reaction.

According to a further advantageous embodiment of the invention, the acid used is a strongly acidic organic cation exchanger, for example an exchanger resin bearing sulfonic acid groups. These ion exchangers are either suspended in the reaction mixture, or arranged as a fixed bed, in each case using conventional methods.

The process according to the invention is preferably carried out with substantial exclusion of water, in particular in the absence of water, ie. using acids which contain virtually no water. It may be carried out in the presence or absence of a non-aqueous solvent, eg. benzene, methylcyclohexane, acetic acid, methanol, methyl acetate, nitrobenzene, chlorobenzene, dichlorobenzene or an aliphatic chlorohydrocarbon.

The reaction, which is complete after from 0.5 to 20 hours, is in general carried out either by slowly adding the acylal to a mixture of the carbamic acid ester and the acid whilst stirring at the reaction temperature, or by heating a mixture of the carbamic acid ester, the acylal and the acid, whilst stirring; in each case the mixture is kept at the reaction temperature for the appropriate time. The reaction product is isolated by conventional methods, for example by extracting the acid with water or by neutralizing it with a base. Any solvent present, and unconverted starting materials, are subsequently removed by distillation under reduced pressure.

The condensation of the phenylcarbamic acid ester with the acylal can be carried out batchwise or continuously.

An essential difference between the process according to the invention and the processes of U.S. Pat. No. 2,946,768 and of German Laid-Open Application DOS No. 2,832,379, in which formaldehyde or a formaldehyde donor is used, so that there is always water present in the reaction mixture, is that in the process according to the invention no formaldehyde is present and hence no water of reaction is formed. Accordingly, any hydrolysis of the carbamic acid esters to give amines, the formation of ureas, and the resulting pollution of effluent, are prevented. Surprisingly, there is also no acylation at the N atom of the carbamic acid ester, even though an acylal is used.

EXAMPLE 1 (COMPARATIVE EXAMPLE)

Following the method of Example 2 in German Pat. No. 1,042,891, a mixture of 183 parts of methyl phenylcarbamate, 500 parts of water and 86 parts of 30% strength formaldehyde solution is heated to 100° C., whilst stirring. 119 parts of concentrated hydrochloric acid are then added. Thereafter, the reaction mixture is stirred for 20 hours at 100° C. After completion of the reaction, the aqueous phase is separated off. The reaction product is washed three times with hot water, after which uncoverted starting material is distilled off under reduced pressure. The residue is analyzed by high-pressure liquid chromatography (HPLC). It contains 50% of methylene-bis-phenylcarbamic acid methyl ester, 9% of trinuclear product, 16% of N-C-bonded binuclear product and 10% of N-C-bonded trinuclear product. The remainder consists of compounds, not identified in more detail, with more than three benzene nuclei per molecule.

EXAMPLE 2 (COMPARATIVE EXAMPLE)

A mixture of 90 parts of methyl phenylcarbamate, 250 parts of chlorobenzene and 40 parts of 30% strength formaldehyde solution is heated to 100° C., whilst stirring, and 59.5 parts of concentrated hydrochloric acid are added. The reaction mixture is then stirred for 20 hours at 100° C. After completion of the reaction, the aqeuous phase is separated off and washed twice with water. Chlorobenzene and unconverted starting material are then distilled off. According to HPLC analysis, the residue contains 49% of methylene-bis-phenylcarbamic acid methyl ester, 12% of trinuclear product, 15% of N-C-bonded binuclear product and 9% of N-C-trinuclear product. The remainder consists of compounds, not identified in more detail, with more than three benzene nuclei per molecule.

EXAMPLE 3

A mixture of 151 parts of methyl phenylcarbamate, 66 parts of diacetoxymethane, 100 parts of nitrobenzene and 20 parts of trifluoromethanesulfonic acid is heated, in a stirred reactor, to 100° C. whilst being stirred. Stirring is then continued for 5 hours at the same temperature. After completion of the reaction, the solvent and uncoverted starting material are distilled off under reduced pressure. 149 parts of a distillation residue are obtained, consisting, according to HPLC analysis, of 71 parts of methylene-bis-phenylcarbamic acid methyl ester, 20% of trinuclear product and 9% of products with more than three benzene nuclei in the molecule.

EXAMPLE 4

A mixture of 302 parts of methyl phenylcarbamate, 44 parts of diacetoxymethane and 50 parts of LEWASORB AC-10 is heated, in a stirred reactor, to 110° C. whilst being stirred. Stirring is then continued for 5 hours at the same temperature. After completion of the reaction, the catalyst is separated off and uncoverted starting material, and the acetic acid formed, are distilled off under reduced pressure. The distillation residue is recrystallized from toluene. 90 parts of methylene-bis-(4-phenylcarbamic acid methyl ester) are obtained. LEWASORB AC-10 is a commercial gel-like cation exchanger, with sulfonic acid groups, based on a copolymer of styrene with 8% of divinylbenzene; it has a particle size of from 0.01 to 0.2 mm and a total capacity of about 4.2 milliequivalent/g of dry material.

EXAMPLE 5

A mixture of 151 parts of methyl phenylcarbamate, 66 parts of diacetoxymethane, 120 parts of nitrobenzene and 50 parts of LEWATIT SPC-108 is heated, in a reactor, to 100° C. whilst being stirred. Stirring is then continued for 5 hours at the same temperature. After completion of the reaction, the catalyst is separated off, after which nitrobenzene and unconverted starting material are distilled off under reduced pressure. 142 parts of a distillation residue are obtained, consisting, according to HPLC analysis, of 76% of methylene-bis-phenylcarbamic acid methyl ester, 16% of trinuclear product and 8% of products with more than three benzene nuclei in the molecule.

We claim:

1. A process for preparing methylene-bis-phenylcarbamic acid esters and polymethylene-polyphenylcarbamic acid esters, wherein an N-phenylcarbamic acid ester is reacted with an acylal of the formula $$CH_2(OCOR)_2$$

where R is alkyl, in the presence of an acid at from 50° to 150° C.

2. A process as claimed in claim 1, wherein the reaction is carried out in the absence of water.

3. A process as claimed in claim 1, wherein trifluoromethanesulfonic acid is used as the acid.

4. A process as claimed in claim 1, wherein a strongly acidic organic cation exchanger is used as the acid.

* * * * *